(12) United States Patent
Zhuo (10) Patent No.: US 9,963,457 B2
(45) Date of Patent: May 8, 2018

(54) CRYSTAL OF 5-((2-(6-AMINO)-9H-PURIN-9-YL)ETHYL)AMINO)PENTAN-1-O1

(71) Applicant: FOREVER CHEER INTERNATIONAL LIMITED, Hong Kong (CN)

(72) Inventor: Min Zhuo, Hong Kong (CN)

(73) Assignee: FOREVER CHEER INTERNATIONAL LIMITED, HONG KONG (CN)

( * ) Notice: Subject to any disclaimer, the term of this patent is extended or adjusted under 35 U.S.C. 154(b) by 0 days. days.

(21) Appl. No.: 15/651,564

(22) Filed: Jul. 17, 2017

(65) Prior Publication Data
US 2018/0030058 A1    Feb. 1, 2018

(30) Foreign Application Priority Data

Aug. 1, 2016   (JP) ................. 2016-151029

(51) Int. Cl.
*C07D 487/04*    (2006.01)
*C07D 473/34*    (2006.01)

(52) U.S. Cl.
CPC ........ *C07D 487/04* (2013.01); *C07B 2200/13* (2013.01)

(58) Field of Classification Search
None
See application file for complete search history.

(56) References Cited

FOREIGN PATENT DOCUMENTS

WO    WO-2007041863 A1 *    4/2007   ............. A61K 31/52

* cited by examiner

*Primary Examiner* — Deepak R Rao
*Assistant Examiner* — Laura M Daniel
(74) *Attorney, Agent, or Firm* — Juan Carlos A. Marquez; Marquez IP Law Office, PLLC (57) ABSTRACT

The present invention provides a new crystal form of 5-((2-(6-amino)-9H-purin-9-yl)ethyl)amino)pentan-1-ol, which has a relatively better effect in selectively inhibiting adenylate cyclase 1 and is capable of preparing a medicament for treating neuropathic pain and/or inflammatory pain.

17 Claims, 5 Drawing Sheets

CRYSTAL OF 5-((2-(6-AMINO)-9H-PURIN-9-YL)ETHYL)AMINO)PENTAN-1-O1

TECHNICAL FIELD

The present invention relates to a polymorphic form of a pharmaceutical compound, and more particularly to a polymorphic form of 5-[2-[(6-amino)-9H-purin-9-yl]ethyl-amino]-1-pentano, which is capable of selectively inhibiting adenylate cyclase 1 and can be used for treating neuropathic pain and/or inflammatory pain.

BACKGROUND

Pain is divided into inflammatory pain, neuropathic pain, nociceptive pain, psychotic (psychogenic) pain, etc., depending on the cause. The inflammatory pain is a pain generated as going with inflammation caused by extracorporeal and nociceptive mechanical stimulation, heat stimulation, chemical stimulation, and the like. It is known that when an inflammatory pain occurs, not only inflammatory sites, but also inflammatory cytokines and cyclooxygenase existed in the spinal cord also play important roles. Neuropathic pain is a pathological pain caused by dysfunction of the peripheral or central nervous system itself. The psychotic pain is a pain generated due to an injury of a normal tissue or the application of a nociceptive stimulation which possibly causes an injury of a normal tissue, and is divided into bodily pain and visceral pain.

As a therapeutic agent for inflammatory pain, a cyclooxygenase (COX) inhibitor such as indomethacin, a cyclooxygenase II (COX-II) inhibitor such as celecoxib, a central analgesic such as tramadol, an analgesic-antipyretic agent such as paracetamol, and the like may be used. However, if the cyclooxygenase inhibitor is used for a prolonged period, as a side effect sometimes gastrointestinal disturbance may be caused, which is problematic. Additionally, as reported the cyclooxygenase II inhibitor may also cause gastric ulcer, and recently its side effects in heart circulation system, such as myocardial infarction, cerebral infarction and the like, also come as problem issues.

As a therapeutic agent for neuropathic pain, a papaverine-like analgesic such as morphine, an anticonvulsive drug such as gabapentin and pregabalin may be used, but it is known that along with the prolonged use time, it is sometimes necessary to increase the dosage and thus a side effect such as sedation may be caused. Currently there are no existing pharmaceutical agent which can be administrated safely without any side effect.

The patent literature 1 (WO2007/041863) described that ol 5-(((2-(6-amino)-9H-purin-9-yl)ethyl)amino)pentan-1-ol is capable of selectively inhibiting adenylate cyclase 1 and can be used for treating neuropathic pain and/or inflammatory pain. However, the patent literature 1 did provide neither a method suitable for preparing ol 5-(((2-(6-amino)-9H-purin-9-yl)ethyl)amino)pentan-1-ol for industrial application, nor a crystal form suitable for pharmaceutical preparation. Moreover, in respect of residual organic solvent in the final product, in different preparation and crystallization methods it is desirable to avoid the use of two or more types of organic solvents harmful to mammals, thereby reducing the adverse effect of residual organic solvent on the user.

For the polymorphic form of a medicament, different polymorphic forms may have different chemical and physical properties, including the melting point, chemical stability, apparent solubility, dissolution rate, optical and mechanical properties, vapor pressure, density and the like. These properties may directly or indirectly affect the processing or production of bulk pharmaceutical chemicals and formulations, and may also affect the stability, solubility and bioavailability of the formulations. Thus, the polymorphic form of the medicament is important for the quality, safety and efficacy of the pharmaceutical formulation. For ol 5-(((2-(6-amino)-9H-purin-9-yl)ethyl)amino)pentan-1-ol, the requirement thereof in the art is: having a polymorphic form which is suitable for industrial production and has excellent physicochemical properties.

Literature of Prior Art

Patent literature 1 WO2007/041863

SUMMARY

The polymorphism in pharmaceuticals is one of essential factors which affect the pharmaceutical quality and clinically therapeutic effect. The patent literature 1 (WO2007/041863) described that the ol 5-(((2-(6-amino)-9H-purin-9-yl)ethyl)amino)pentan-1-ol is capable of selectively inhibiting adenylate cyclase 1 and can be used for treating neuropathic pain and/or inflammatory pain, but provided no crystal of ol 5-(((2-(6-amino)-9H-purin-9-yl)ethyl)amino)pentan-1-ol applicable to clinical application.

Therefore, the present invention is directed to provide a crystal of ol 5-(((2-(6-amino)-9H-purin-9-yl)ethyl)amino)pentan-1-ol for use in a medicament for the treatment of neuropathic pain and/or inflammatory pain, which has excellent performance in efficacy and safety.

Additionally, through extensive studies, the inventor surprisingly finds a synthesis route of ol 5-(((2-(6-amino)-9H-purin-9-yl)ethyl)amino)pentan-1-ol and obtains a new crystal form, which successfully solves the problems existed in the prior art. The new crystal form has advantages of excellent physicochemical properties, great stability, and being more suitable for industrial preparation.

The present invention provides a crystal of ol 5-(((2-(6-amino)-9H-purin-9-yl)ethyl)amino)pentan-1-ol, which as the following data of powder x ray diffraction:

the crystal is measured by using Cu-Ka and shows a characteristic peak at an interplanar crystal spacing d of 13.8°±0.2°, 16.0°±0.2°, 17.1°±0.2°, 21.6°±0.2°, 22.1°±0.2°, 22.5°±0.2°, 23.7°±0.2°, 24.7°±0.2° and 31.7°±0.2° in powder x ray diffraction.

The present invention provides a synthesis route of ol 5-(((2-(6-amino)-9H-purin-9-yl)ethyl)amino)pentan-1-ol as below:

-continued

NB001

The present invention also provides a medicament containing the new crystal of ol 5-(((2-(6-amino)-9H-purin-9-yl)ethyl)amino)pentan-1-ol as provided by the present invention.

The medicament provided by the present invention is an inhibitor of adenylate cyclase 1.

The medicament provided by the present invention is an analgesic.

The medicament provided by the present invention is a medicament for the treatment of neuropathic pain and/or inflammatory pain.

The medicament provided by the present invention is a medicament for the treatment of cancerous pain.

The medicament provided by the present invention is a medicament for the treatment of anxiety caused by the neuropathic pain and other disease-related anxiety and depression.

The medicament provided by the present invention is a medicament for the treatment of chronic visceral pain and anxiety and depression associated thereto.

The present invention also provides the use of the crystal of ol 5-(((2-(6-amino)-9H-purin-9-yl)ethyl)amino)pentan-1-ol in the manufacture of a medicament for the treatment of neuropathic pain and/or inflammatory pain.

The present invention also provides the use of the crystal of ol 5-(((2-(6-amino)-9H-purin-9-yl)ethyl)amino)pentan-1-ol in the manufacture of a medicament for the treatment of anxiety caused by the neuropathic pain and other disease-related anxiety and depression.

The present invention also provides the use of the crystal of ol 5-(((2-(6-amino)-9H-purin-9-yl)ethyl)amino)pentan-1-ol in the manufacture of a medicament for the treatment of chronic visceral pain and anxiety and depression associated thereto.

The present invention also provides the use of the crystal of ol 5-(((2-(6-amino)-9H-purin-9-yl)ethyl)amino)pentan-1-ol in the treatment of neuropathic pain and/or inflammatory pain.

The present invention also provides the use of the crystal of ol 5-(((2-(6-amino)-9H-purin-9-yl)ethyl)amino)pentan-1-ol in treatment of anxiety caused by the neuropathic pain and other disease-related anxiety and depression.

The present invention also provides the use of the crystal of ol 5-(((2-(6-amino)-9H-purin-9-yl)ethyl)amino)pentan-1-ol in the treatment of chronic visceral pain and anxiety and depression associated thereto.

DETAILED DESCRIPTION

The ol 5-(((2-(6-amino)-9H-purin-9-yl)ethyl)amino)pentan-1-ol of the present invention has the following structure:

5-(((2-(6-amino)-9H-purin-9-yl)ethyl)amino)pentran-1-ol

This compound is numbered as NB001 in the present invention.

The compound NB001 of the present invention can be synthesized and purified through the following scheme.

NB001

Compound 1 is 2-(6-Aminopurin-9-yl)ethanol, a commercially available product from e.g., J&K Scientific, Meryer (Shanghai) Chemical Technology Co., Ltd., or INTA-TRADE GmbH of Germany, and in the embodiments of the present invention the compound 1 is purchased from Cool Pharm.

Compound 3 is 5-Amino-1-pentanol, a product available from Wako Pure Chemical Industries, Ltd. or HBCChem, Inc., and the compound 3 of the present invention is purchased from TCI.

A compound 2 is prepared through a substitution reaction of the compound 1 with thionyl chloride in accordance with the afore-mentioned scheme. The substitution reaction is carried out in a conventional manner or in a solvent which does not affect the reaction.

By way of example, the solvent which does not affect the reaction may include: ethers such as dioxane, tetrahydrofuran, 1,2-dimethoxyethane and the like; halogenated hydrocarbons such as chloroform; aromatic hydrocarbons such as toluene; amides such as N,N-dimethylformamide; and sulfoxides such as dimethyl sulfoxide and the like. More than two of these solvents may be mixed in an appropriate ratio when used. The amount of these solvents is, for example, 1 to 100 times by volume of the compound 1.

The reaction temperature is generally about 20° C. to about 250° C., and preferably 20° C. to 120° C.

The reaction time is generally about 0.5 to about 36 hours.

The compound 2 obtained in such a manner can be isolated and purified by a well-known separation and purification method such as concentration, concentration under reduced pressure, solvent extraction, crystallization, recrystallization, phase transfer, chromatography and the like. It should be noted that compound 2 can be used directly in subsequent reactions without isolation.

Next, compound 2 is subjected to a condensation reaction with compound 3 to obtain the compound NB001 of the present invention.

The reaction is carried out in a conventional manner and in a solvent which does not affect the reaction.

By way of example, the solvent which does not affect the reaction may include: hydrocarbons such as hexane and the like; alcohols such as methanol and the like; ethers such as tetrahydrofuran and the like; esters such as ethyl acetate and the like; halogenated hydrocarbons such as chloroform; aromatic hydrocarbons such as toluene; amides such as N,N-dimethylformamide; and sulfoxides such as dimethyl sulfoxide and the like. More than two of these solvents may be mixed in an appropriate ratio when used. The amount of these solvents is, for example, 2 to 100 times by volume of the compound 1.

The reaction temperature is usually about 20° C. to about 250° C., and preferably 20° C. to 120° C.

The reaction time is generally about 0.5 to about 24 hours.

The compound NB001 obtained in such a manner can be isolated and purified by a well-known separation and purification method such as concentration, concentration under reduced pressure, solvent extraction, crystallization, recrystallization, phase transfer, chromatography and the like. It should be noted that compound NB001 can be used directly in subsequent reactions without isolation.

Examples of the solvate crystals of the compound NB001 include, for example, alcohol solvate crystals such as methanol solvate crystals, ethanol solvate crystals and the like; organic solvent hydrate crystals having water and an organic solvent (e.g., alcohol solvate hydrate crystals, such as methanol hydrate crystallization, ethanol hydrate crystallization, etc.); and the like.

The crystal of the present invention can be produced by subjecting the amorphous compound NB001, or other crystal forms of the compound NB001, to a crystal transition. The change in crystal form is a phenomenon in which the crystal structure changes when the temperature or pressure exceeds a certain level.

Examples of the crystal transition method include a method known per se, for example, by crystallization of solution (e.g., a concentration method, a slow cooling method, a reaction method (a diffusion method, and an electrolysis method), a hydrothermal growth method, and a flux method), by vapor crystallization (e.g., a gasification process (a pipe sealing method, and an airflow method), a vapor reaction method, and a chemical transport method), by a melt crystallization method (e.g., a conventional freezing method (a lifting method, a temperature gradient method, and a Bridgman method), a zone melting method (a zone leveling method, and a floating zone method), a special growth method (a VLS method, a liquid phase epitaxy method), a stream fog method (wherein the crystal is dissolved in a solvent, filtered, and the solvent is evaporated under atmospheric conditions), a slurry method (wherein the crystal is added to a solvent such that an excess amount of solid is retained therein to obtain a suspension, the suspension is stirred at room temperature or under a heating or cooling condition, and then the solid is collected by filtration), and methods such as drying under reduced pressure, grinding, pulverization, pressurization and the like.

For obtaining the crystal of the present invention, the slurry method is particularly preferred among the aforementioned methods. Specifically, the method is preferably as follows: adding the crystal of the compound NB0011 into a solvent such that an excess amount of solid is retained therein to obtain a suspension, stirring the suspension, and collecting the solid by filtration. The solvent as used includes, for example, aromatic hydrocarbons (e.g., benzene, toluene, xylene, etc.), halogenated hydrocarbons (e.g., dichloromethane, chloroform, etc.), saturated hydrocarbons (e.g., hexane, heptane, cyclohexane, etc.), ethers (e.g., diethyl ether, diisopropyl ether, tetrahydrofuran, dioxane, etc.), nitriles (e.g., acetonitrile, etc.), ketones (e.g., acetone, etc.), sulfoxides (e.g., dimethylsulfoxide, etc.), amides (e.g., N,N-dimethylformamide, etc.), esters (e.g., ethyl acetate, etc.), alcohols (e.g., methanol, ethanol, 2-propanol, etc.), water and the like. These solvents may be used alone or in combination of two or more in an appropriate ratio (e.g., 1:1 to 1:100). The solvent is preferably alcohols (e.g., 2-propanol, etc.), ketones (methyl ethyl ketone, etc.) and esters (e.g., ethyl acetate, etc.), and more preferably ketones (methyl ethyl ketone, etc.).

The amount of the solvent as used is generally about 5 mL to about 65 mL, and preferably about 5 mL to about 25 mL, relative to the crystal of compound NB001 (1 g).

The suspension is preferably stirred at room temperature or from about 30° C. to about 60° C., and more preferably from about 30° C. to about 60° C. In the present specification, room temperature refers to a temperature of about 15° C. to about 30° C. The stirring time at about 30° C. to about 60° C. is generally about 30 minutes to about 4 hours, and preferably about 2 hours to about 4 hours. The cooling temperature is room temperature. The stirring time under the cooling condition is generally from about 30 minutes to about 24 hours, and preferably from about 30 minutes to about 2 hours. The crystals from the suspension can be separated by methods known per se such as filtration or the like. The filtration temperature is room temperature, and preferably about 20° C. to about 30° C.

Alternatively, A method in which the suspension is stirred at about 0° C. to about 10° C., and then filtered at about 0° C. to about 10° C. to collect the crystal may be adopted.

The obtained crystal may be dried by a method known per se to obtain the crystal of the present invention. The drying may be carried out by reducing the pressure or by ventilation. The drying temperature is preferably no higher than about 60° C., and more preferably about 45° C. to about 55° C.

The crystal other than the crystal of the present invention can be prepared by other known methods.

In order to analyze the obtained crystal, an X-ray diffraction crystallization analysis method is generally used. Furthermore, the crystal orientation can also be determined by a mechanical or optical method (e.g., FT-Raman spectroscopy, solid-state NMR spectroscopy, etc.).

The peaks of the spectra obtained through the aforementioned analysis method inevitably produce a certain determination error in nature. A crystal having a spectral peak within the error range is also encompassed in the concept of crystal of the present invention. For example, "±0.2" in the description of the interplanar crystal spacing (d) of the powder X-ray diffraction means that the error can be allowed.

EMBODIMENTS

Embodiment 1: Synthesis of Compound NB001

The compound NB001 was synthesized according to the following synthetic route.

Synthesis and Purification of Intermediate 2

The compound 1 (20.00 g, 111.62 mmol, 1.00 eq) was dissolved in dioxane (600.00 mL), and then $SOCl_2$ (26.56 g, 223.24 mmol, 16.20 mL, 2.00 eq) was slowly added to the afore-mentioned reaction solution, and the mixture was continuously stirred at 100° C. for 4 hours. The LCMS assay showed the raw materials are reacted completely and the desired product was generated. The solvent in the reaction solution was removed under reduced pressure in a water pump. The gray residue was added into 100 ml of ethanol and stirred for 10 minutes. The mixture was filtered through a sintered glass funnel. 100 ml of saturated sodium carbonate solution was added to the filtered solid and stirred for 20 minutes. The mixture was filtered through a sintered glass funnel. The filtered solid was spin-dried in a water pump under reduced pressure to obtain crude intermediate 2 (19.60 g, 98.59 mmol, with a yield of 88.32% and a purity of 99.4%), and the product is directly used in the next step without further purification.

(2) Synthesis and Purification of NB001

The compound 2 (19.60 g, 99.18 mmol, 1.00 eq) was dissolved in n-BuOH (390.00 mL), and then the compound 3 (30.69 g, 297.54 mmol, 3.00 eq) was slowly added to the afore-mentioned reaction solution, and the mixture was continuously stirred at 110° C. for 18 hours. The LCMS assay showed the raw materials are reacted completely and the desired product was generated. The solvent was removed under reduced pressure through a water pump, and the residue was concentrated to obtain a yellow crude product. 196 ml of DMF was added into the yellow crude product, then the mixture was continuously stirred at −40° C. for 1 hour. Then the mixture was filtered through a sintered glass funnel. 200 ml of ethyl acetate was added into the filtered solid, and the mixture was filtered again to obtain an off-white solid NB001 (19.74 g, 71.38 mmol, with a yield of 71.97% and a purity 95.587%).

Example 2: Preparation of New Crystal Form of NB001

Into 7 mL vials were weighed 2.0 mg of the raw material respectively. Then appropriate amount of methanol, ethanol, isopropyl alcohol, n-butanol, acetonitrile, acetone, ethyl acetate, 2-methyl tetrahydrofuran, tetrahydrofuran, dioxane, n-pentyl alcohol, toluene, isopropyl alcohol+water (with a mass ratio of 3:1), acetonitrile+water (with a mass ratio of 3:1), acetone+water (with a mass ratio of 3:1), and ethanol+water (with a mass ratio of 3:1) were added into respective vials, and the mixture was shaken rapidly to dissolve the compound of the mixture until the solution becomes clear. The approximate solubility of the resultant bulk pharmaceutical chemicals (BPC) in an organic solvent and a mixed solvent was shown in Table 1 below.

TABLE 1

Approximate Solubility of BPCs in Organic Solvent and Mixed Solvent

| No. | Solvent | BPCs (mg) | Approximate Solubility |
|---|---|---|---|
| 1 | tetrahydrofuran | 2.19 | <2 |
| 2 | acetonitrile | 1.97 | <2 |
| 3 | acetone | 2.13 | <2 |
| 4 | methanol | 2.12 | 50~66 |
| 5 | ethanol | 2.0 | 7~10 |
| 6 | n-butanol | 2.17 | 2.2~2.5 |
| 7 | toluene | 1.95 | <2 |
| 8 | isopropyl alcohol | 1.96 | 2.0 |
| 9 | n-pentyl alcohol | 1.96 | 3~4 |
| 10 | dioxane | 2.07 | <2 |
| 11 | 2-methyl tetrahydrofuran | 2.19 | <2 |
| 12 | ethyl acetate | 2.09 | <2 |
| 13 | isopropyl alcohol/water | 2.16 | 70~100 |
| 14 | acetonitrile/water | 2.01 | 100~200 |
| 15 | acetone/water | 2.12 | 100~200 |
| 16 | ethanol/water | 2.15 | 100~200 |

Into 2 mL vials were weighed 50 mg BPCs according to Table 2 respectively. Then appropriate amount of acetonitrile, tetrahydrofuran, acetone, isopropyl alcohol, ethyl acetate, and ethanol were added into respective vials to obtain a suspension. The suspension was stirred in a mixer under a condition of 40° C. for two days, and then dried by baking at 40° C. after centrifugation. Methanol, ethanol+water (with the mass ratio of 3:1), isopropanol+water (with the mass ratio of 3:1), and acetonitrile+water (with the mass ratio of 3:1) were naturally evaporated 3 days after complete dissolution. The resultant solids were subjected to XRPD respectively and then compared with the XRPD of BPCs.

Figure 1:
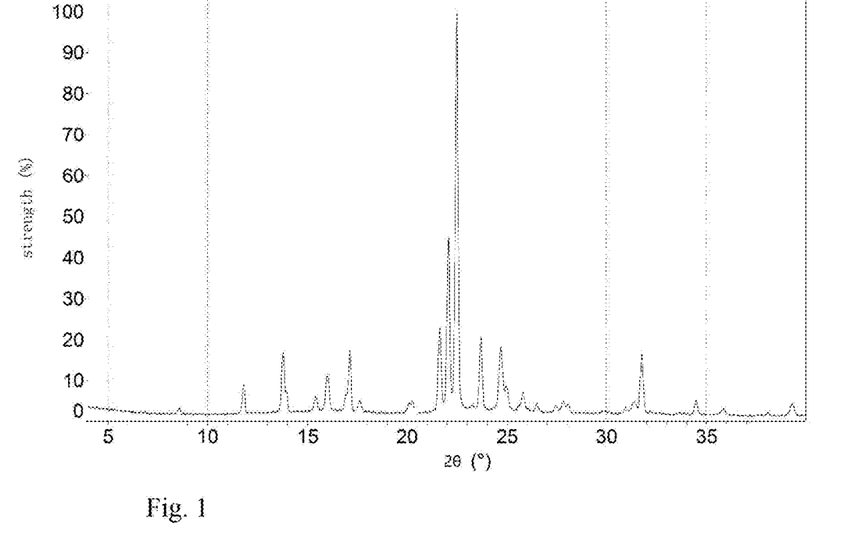
FIG. 1 is an XRPD of the crystal involved in the embodiments of the present invention.

The X-ray powder diffractometer (XRPD) as used is the PANalytical Empyrean, with specific parameters of: tube: copper: K-Alpha ($\lambda$=1.54179 Å); generator: voltage: 40 kV, current: 40 mA; scanning range: 4-40 degrees; sample rotation speed: 15 rpm; scanning speed: 10 degrees/min, and the results were as shown in FIG. 1.

TABLE 2

Proportioning of Solutions Used in Crystallization of BPCs

| No. | Solvent used | Weight (mg) | Volume of solvent (ml) | Heating Temperature |
|---|---|---|---|---|
| 1 | acetonitrile | 52.2 | 1.0 | 40° C. |
| 2 | tetrahydrofuran | 51.7 | 1.0 | 40° C. |
| 3 | acetone | 50.5 | 1.0 | 40° C. |
| 4 | methanol | 51.2 | 1.0 | 40° C. |
| 5 | isopropyl alcohol | 52.4 | 1.0 | 40° C. |
| 6 | ethyl acetate | 51.8 | 1.0 | 40° C. |
| 7 | ethanol | 51.2 | 1.0 | 40° C. |
| 8 | ethanol + water | 50.9 | 1.0 | 40° C. |
| 9 | acetonitrile + water | 51.8 | 1.0 | 40° C. |
| 10 | isopropyl alcohol + water | 50.1 | 1.0 | 40° C. |

TABLE 3

Powder X-ray Diffraction Data

| 2θ | D value (angstrom) | Relative strength (%) |
|---|---|---|
| 13.8° ± 0.2° | 6.41 | 17.4 |
| 16.0° ± 0.2° | 5.53 | 12.8 |
| 17.1° ± 0.2° | 5.17 | 14.3 |
| 21.6° ± 0.2° | 4.10 | 20.6 |
| 22.1° ± 0.2° | 4.02 | 47.7 |
| 22.5° ± 0.2° | 3.95 | 100.0 |
| 23.7° ± 0.2° | 3.75 | 17.6 |
| 24.7° ± 0.2° | 3.59 | 27.6 |
| 31.7° ± 0.2° | 2.81 | 25.2 |

Example 3: Other Physical Properties of New Crystal Form of NB001

The physical characterization of the BPCs was determined using PLM, TGA, DSC, and DVS. The results are shown in FIGS. 1 to 5.

(1) Polarized Light Microscope (PLM)

Figure 2:
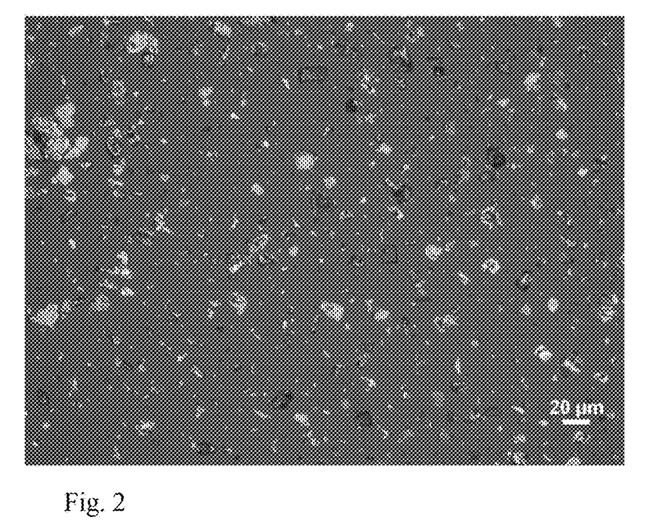
FIG. 2 is a photograph of the crystal involved in the embodiment of the present invention under a polarizing microscope.

The solid samples were dispersed in silicone oil and observed under a PLM using a 10× ocular lens and a 20/50× object lens. The microscope as used is Polarized Light Microscope-Nikon Eclipse LV 100POL from Nikon, and the images of the samples under the 20× object lens of this microscope were as shown in FIG. 2.

Figure 3:
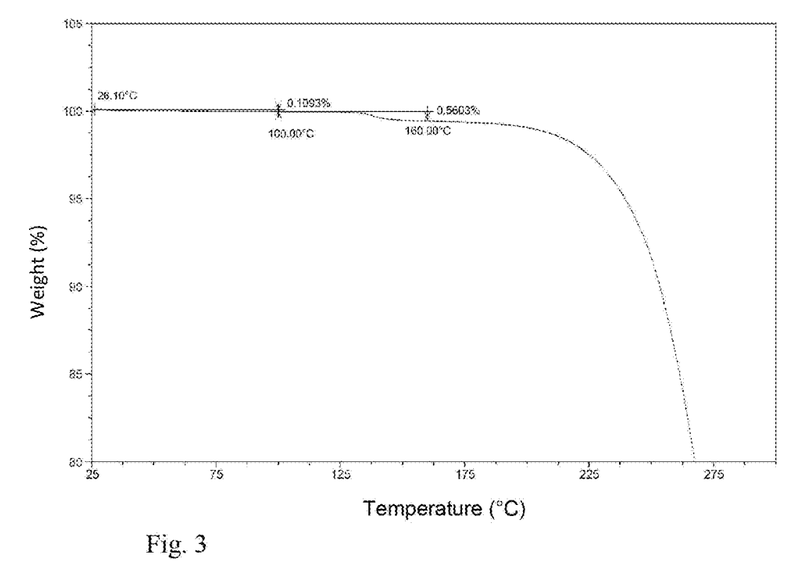
FIG. 3 is a TGA plot of the crystal involved in the embodiments of the present invention.

(2) Thermogravimetric Analyzer (TGA) Assay 2 to 5 mg of the samples were placed in sample trays and heated from room temperature to 300° C. at a rate of 10° C./min. The results were as shown in FIG. 3.

(3) Differential Scanning calorimetry (Dsc) Assay

Figure 4:
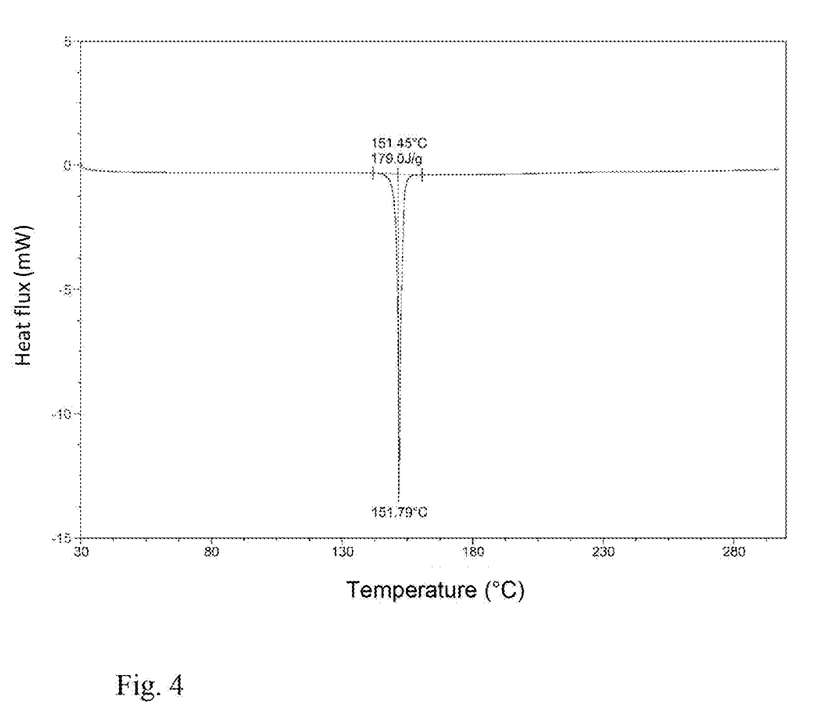
FIG. 4 is a DSC plot of the crystal involved in the embodiments of the present invention.

DSC Assay: appropriate amount of samples was placed in specific aluminum trays and heated from 25° C. to 300° C. at 10° C./min. The results were as shown in FIG. 4.

(4) Dynamic Vapor Adsorption (DVS)

Onto the sample trays were weighed about 20 mg of samples, and then the sample trays are put into the instrument for testing.

Figure 5:
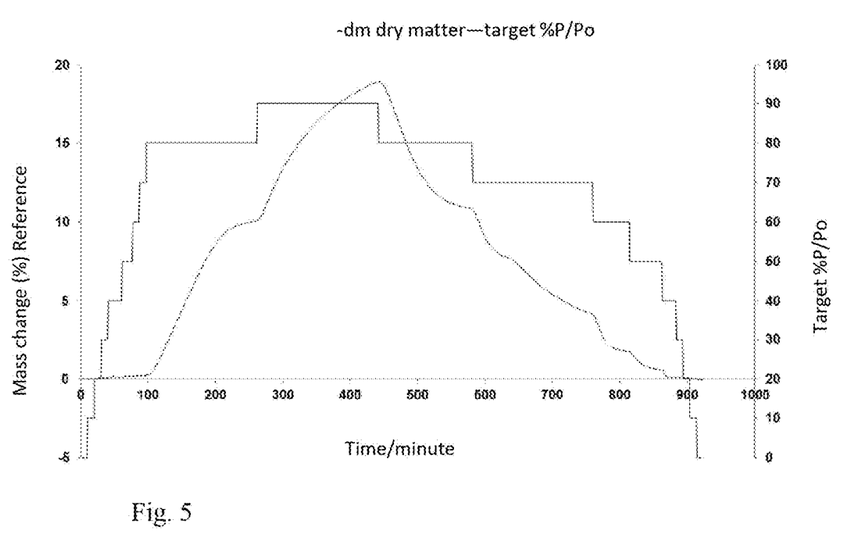
FIG. 5 is an adsorption-desorption curve cycle 1 of the crystal involved in the embodiments of the present invention, showing the water adsorption kinetics of the crystal at 25° C.
Figure 6:
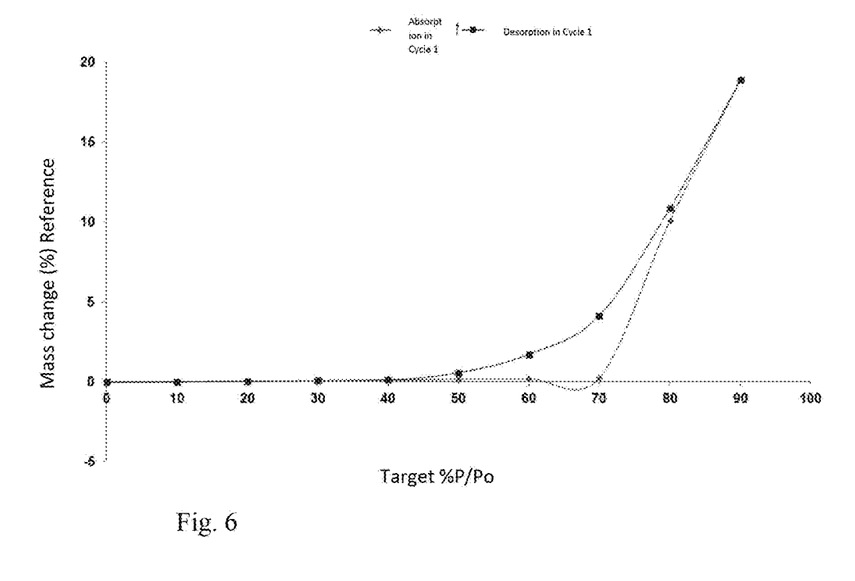
FIG. 6 is the adsorption/desorption isothermal cycle of the crystal involved in the embodiments of the present invention, showing the water adsorption kinetics of the crystal at 25° C.

The parameters are as follows:
Temperature: 25° C.
Balance: dm/dt: 0.01%/min (the shortest: 10 min, the longest: 180 min)
Drying: for 120 min under 0% RH
RH (%) Test Gradient: 10%
range of RH (%) Test Gradient: 0%-90%-0%
The DVS results are as shown in FIGS. 5 and 6.

Example 4: Stability of Crystal Form of NB001

Stress test, long-term stable test and accelerated stability test of the compound with the crystal form:

The stability of the compound with such a crystal form was investigated under conditions of a high temperature (60° C.), high humidity (92.5% RH), strong light irradiation (5 Klx), 40° C./75% RH (for accelerated test) and 25° C./60% RH (for long term test), in accordance with "Guidelines for Stability Testing of bulk pharmaceutical chemicals and formulation" (Chinese Pharmacopoeia 2015 Edition, four main sections of general requirements 9001).

10 mg of the crystalline sample involved in the Examples of the present invention was accurately weighed and placed on the bottom of a glass sample vial, and then spread out to form a thin layer. The samples for test under high temperature and high humidity conditions and for the long-term test were contained in vials sealed with aluminum-foil paper, and some small holes were made on the aluminum-foil paper to ensure that the sample can be fully in contact with ambient conditions; The samples for test under strong light irradiation and for the accelerated test were contained in vials sealed with screw bottle caps. The conditions and timing for sample placing were shown in Table 4. The samples placed under different conditions were taken and analyzed on day 5, 10, and 30, and the analysis results were compared with the initial test results on day 0. The results of the stability test were shown in Table 5.

TABLE 4

Conditions and timing for sample placing of the stability test of the crystals involved in Examples of the present invention

| Test items and Test Conditions | | 5 Days | 10 Days | 30 Days |
|---|---|---|---|---|
| Stress Test | High temperature (60° C., open) | X* | X | X |
| | High Humidity (92.5% RH, open) | X | X | X |
| | Strong Light Irradiation (5 Klx, sealed) | — | X | — |
| | Long-Term Test (25° C./60% RH, sealed) | — | — | X |

TABLE 4-continued

Conditions and timing for sample placing of the stability test of the crystals involved in Examples of the present invention

| Test items and Test Conditions | 5 Days | 10 Days | 30 Days |
|---|---|---|---|
| Accelerated Test (40° C./75% RH, open) | — | — | X |

TABLE 5

Results of stability test of the crystals involved in Examples of the present invention

| Test items and Test Conditions | | Time Points | Characteristics | Content (%) | Total Impurities (%) |
|---|---|---|---|---|---|
| — | | Day 0 | off-white powder | 99.39 | 0.61 |
| Stress Test | High temperature (60° C.) | Day 5 | off-white powder | 99.47 | 0.53 |
| | | Day 10 | off-white powder | 99.52 | 0.48 |
| | | Day 30 | off-white powder | 99.43 | 0.57 |
| | High Humidity (92.5% RH) | Day 5 | off-white powder | 99.51 | 0.49 |
| | | Day 10 | off-white powder | 99.41 | 0.59 |
| | | Day 30 | off-white powder | 99.53 | 0.47 |
| | Strong Light Irradiation (5 Klx) | Day 10 | off-white powder | 99.48 | 0.52 |
| Long-Term Test (25° C./60% RH) | | Day 30 | off-white powder | off-white powder | 0.60 |
| Accelerated Test (40° C./75% RH) | | Day 30 | off-white powder | 99.51 | 0.49 |

The above results showed that the stability of the compound with such a crystal form under various test conditions is good.

Example 5: Therapeutic Effect of NB001 Crystal as Analgesic on Cancer Pain in Rats (I) Method:

1. Animals 50 SD rats (180-220 g), placed under a quiet and warm (22° C.) environment without strong light irradiation, having free access to feed and water.

2. Cell Culture: SD Rat homologous cancer cell strains Walker 256 preserved by the Laboratory Animal Center, Forth Military Medical University, or a commercially available product can be used. RPMI 1640 culture medium (Gibco Inc. of US, containing 100 U/ml each of 10% fetal bovine serum, penicillin, and streptomycin) was used, and the tumor cells were incubated as suspension cells in a 37° C. incubator under 5% $CO_2$, with the medium replaced every other day, and 2 days for 1 passage. The cells were harvested at the $3^{rd}$ passage, with a cell concentration of $2 \times 10^5/10$ μl.

3. Establishment of bone cancer pain model in rat: the rats were operated at the left knee with a small incision after anesthesia (40 mg/kg of pentobarbital sodium) according to sterile surgical operation procedures, the muscle was stripped off gently and the patellar ligament is cut open to expose the distal femur, with 1 mm syringe needle inserted from the intercondylar fossa vertically into the marrow cavity, with an inserting distance no more than 5 mm to prevent punching. Then a 20 μl micro-injector was inserted into the marrow cavity to slowly inject 10 μl of a suspension containing the Walker 256 cells ($2 \times 10^5$ cancer cells per 10 μl). The injector was stayed there for a few minutes after the injection, and then the needle pinhole was immediately sealed with sterile bone wax. The tumor cells leaking out of the marrow cavity were killed with 75% ethyl alcohol, and then the rat was sutured under sterile conditions layer by layer. The same operation was performed in the sham operation group, except that only the same volume of sterile saline was injected into the marrow cavity slowly.

4. Imageological examination (X-ray): on day 7, 14, and 21 after the surgical operation, the SD rats was subjected to X-ray radiography of the left lower limb after anesthesia, to assess the degree of tumor-induced bone destruction and hyperostosis response.

5. Histopathological examination (H.E. staining): on day 21 after the modeling operation, the rats were sacrificed after anesthesia. The left femur was fixed in 4% paraformaldehyde liquid for 1 week, then decalcified in a formic acid-hydrochloric acid compound decalcified liquid for 1 week, dehydrated conventionally, embedded in paraffin (Leica), sliced into sections, subjected to a conventional H.E. staining, and then placed under a microscope (Olympus BX53) to observe the destruction conditions of the bone structure.

6. Drug intervention: On day 18 after the surgical operation, the SD rats of the operation group were randomized into 6 groups, i.e., respectively the model group; non-crystalline NB001 group (20 mg/kg, i.g.); the group of the crystal of the present invention (20 mg/kg, i.g.); morphine (2 mg/kg, i.p.); and gabapentin (100 mg/kg, i.g.). The new crystal form and non-crystalline form of the AC1 inhibitor NB001 were both formulated with sterile saline, and morphine and gabapentin were used as positive control drugs. All drugs were administered twice daily for 3 days, and the pain threshold was measured within 2 hours after the last administration on day 3

7. Assessment of rat pain behavior:

Paw withdrawal thermal latency (PWL): the PWL was measured by using a PL-200 thermal pain stimulator (8V, 50 W, with a strength of 100%). The time period since the time irradiating the middle portion of the planta pedis at the operation side of the rat with light till the time the rat lifted its leg to keep out of the light was TWL. To prevent tissue injury, a cut-off time of 80 s was set, each rat was measured for 3 times with an interval of 5 min, and the results were averaged.

Figure 7:
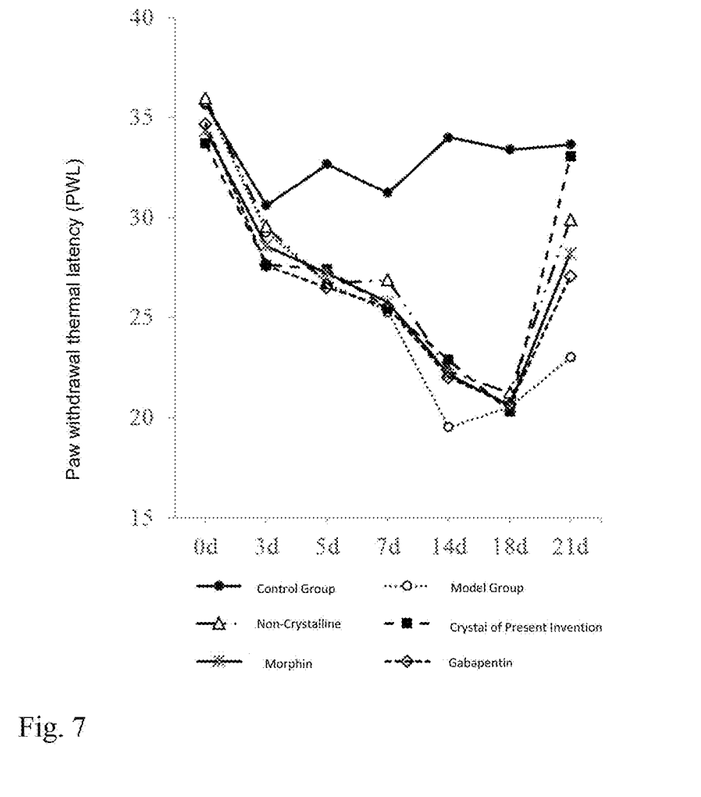
FIG. 7 is a diagram showing the results of pain behavioral test after modeling in rats.

PWL determination at 2 h after the 7th administration (21d): as compared with the model group, the non-crystalline NB001 group (20 mg/kg, i.g.); the group of the crystal of the present invention (20 mg/kg, i.g.); morphine (2 mg/kg, i.p.); and gabapentin (100 mg/kg, i.g.) all had a better analgesic effect, wherein it can be seen from FIG. 7 that the analgesic effect of the group of the crystal of the present invention (20 mg/kg, i.g.) was extremely significant (P<0.01).

Example 6: Effect of NB001 Crystal in Inhibition of Chronic Pain and Anxiety

Chronic Visceral Pain Model

The visceral pain is induced by injecting yeast polysaccharide into the mice colony, and the yeast polysaccharide is derived from *Saccharomyces cerevisiae* (Sigma), wherein one kind of dextran is resident on the cell wall of the yeast and is identified as a protein-carbohydrate complex. Specifically, the mice were anesthetized after inhaling 1-3% isoflurane, and then a 0.1M suspension of yeast polysaccharide (formulated as a 30 mg/ml solution in physiological saline) was injected into the colon of the mice by using a 24 mm long plastic feed needle within 2 minutes. The control group was injected with 0.1 ml physiological saline. The yeast polysaccharide or physiological saline was injected daily for 3 days. A visceral pain behavior test was carried out according to the Laird procedure. The number of times the mice licking the abdomen within 10 minutes was recorded, excluding other grooming behaviors, stretching of whole body, pressing the abdomen against the floor, and an 1-2-second arched posture. On day 1, 7 and 14 after the injection into the colon, an open field test was carried out from 9 am to 12 pm, and the entire test was a double-blind test. Prior to the behavioral test, the mice were acclimated for 30 minutes in an observation room. The mice were placed at the middle of a new open zone (43.2×43.2×30.5 $cm^3$) with micro light (<50 lux) and a fan. The movement distance, vertical count, movement count, stereotypic behavior count, and jumping count of animals were recorded within 30 minutes by means of an activity monitoring system equipped with multiple pairs of packaged light beam sets.

Behavioral Anxiety Test

An anxious animal model of the prior art—the elevated plus maze test (EPM) was adopted. The mice were acclimated for 30 minutes in the room prior to the behavior observation. The EPM was composed of two open arms (250 lux) and two closed arms (350 lux) arranged opposite to each other. For each test, an individual animal was placed at the center of the test position and allowed to move freely. The test is carried out for 5 minutes. The number of entering the test position for each arm and the time spent therefore were recorded.

Bright/dark box test: The test procedure was carried out by using an improved method in accordance with the prior art. The device was composed of a rectangular organic glass box (44×8.5×25 $cm^3$), which is separated into bright and dark compartments with the equal size by using a door. A 60 watt lamp (400 lux) in turn-on state was placed at 30 cm above the box to irradiate the bright compartment. Each animal was first placed in the dark compartment for 20 seconds, and then the door leading to the bright compartment was open. The time each animal stayed in the dark compartment and the time each animal enters the bright compartment within 10 minutes were recorded.

Results

The physiological saline, non-crystalline NB001 (3 mg/kg), the crystal of the present invention (3 mg/kg), and Gabapentin (30 mg/kg) as a positive control were intraperitoneally injected (IP) into the mice treated with yeast polysaccharide respectively. The behaviors of Mice were observed 28 days after the yeast polysaccharide treatment. The results were shown in Table 6, indicating that as compared with the positive control group, the non-crystalline NB001 (3 mg/kg), the crystal of the present invention (3 mg/kg) both had significant therapeutic effects. Furthermore, the therapeutic effect of the group of the crystal of the present invention is extremely significant.

TABLE 6

The therapeutic effect of the crystal of the present invention on chronic pain

| | Number of animals | Number of visceral pain scores |
|---|---|---|
| saline | 8 | 27.5 ± 2.4 |
| Old NB001 | 7 | 19.6 ± 1.2 |
| New NB001 | 8 | 11.0 ± 0.7 |
| Gabapentin | 8 | 20.7 ± 1.9 |

The other two sets of tests were conducted to test the effect of the crystal of the present invention on inhibiting anxiety caused by chronic pain and neuropathic pain.

The EPM test tested the anxiety behavior of mice after the test treatment. The physiological saline, non-crystalline NB001 (3 mg/kg), the crystal of the present invention (3 mg/kg), and Gabapentin (30 mg/kg) as a positive control were intraperitoneally injected (IP) into the mice treated with yeast polysaccharide respectively. The behaviors of Mice were observed 28 days after the yeast polysaccharide treatment. The results were shown in Table 7, indicating that as compared with the positive control group, the non-crystalline NB001 (3 mg/kg), the crystal of the present invention (3 mg/kg) both had significant therapeutic effects. Furthermore, the therapeutic effect of the group of the crystal of the present invention is extremely significant.

TABLE 7

Results of EPM Test

| | Neuropathic pain % time in the open arm | Visceral pain |
|---|---|---|
| Control | 18.6 ± 1.6 (n = 8) | |
| After neuropathic pain or visceral pain | 4.1 ± 1.0 (8) | 4.1 ± 0.8 (6) |
| NB001 | 10.1 ± 1.8 (8) | 5.2 ± 0.7 (8) |
| New NB001 | 18.5 ± 1.4 (8) | 10.3 ± 1.2 (8) |
| Gabapentin | 9.6 ± 1.5 (7) | 8.6 ± 1.5 (8) |

In order to confirm the effect of the crystal of the present invention on inhibiting anxiety, mice were subjected to a bright/dark box test, and the results were as shown in Table 8. The physiological saline, non-crystalline NB001 (3 mg/kg), the crystal of the present invention (3 mg/kg), and Gabapentin (30 mg/kg) as a positive control were intraperitoneally injected (IP) into the mice treated with yeast polysaccharide respectively. The behaviors of Mice were observed 28 days after the yeast polysaccharide treatment. The results were shown in Table 8, indicating that as compared with the positive control group, the non-crystalline NB001 (3 mg/kg), the crystal of the present invention (3 mg/kg) both had significant therapeutic effects. Furthermore, the therapeutic effect of the group of the crystal of the present invention is extremely significant.

TABLE 8

Results of Bright/Dark Box Test

| | Neuropathic pain % time in the open arm | Visceral pain |
|---|---|---|
| Control | 18.6 ± 1.6 (n = 8) | |
| After neuropathic pain or visceral pain | 4.1 ± 1.0 (8) | 4.1 ± 0.8 (6) |
| NB001 | 10.1 ± 1.8 (8) | 5.2 ± 0.7 (8) |
| New NB001 | 18.5 ± 1.4 (8) | 10.3 ± 1.2 (8) |
| Gabapentin | 9.6 ± 1.5 (7) | 8.6 ± 1.5 (8) |

I claim:

1. A crystal of 5-(((2-(6-amino)-9H-purin-9-yl)ethyl)amino)pentan-1-ol, wherein the crystal is measured by using Cu-Ka and shows a characteristic peak at an interplanar crystal spacing d of 13.8°±0.2°, 16.0°±0.2°, 17.1°±0.2°, 21.6°±0.2°, 22.1°±0.2°, 22.5°±0.2°, 23.7°±0.2°, 24.7°±0.2° and 31.7°±0.2° in powder x ray diffraction.

2. The crystal of claim 1, wherein the crystal has the following data of powder x ray diffraction:

| 2θ | D value (angstrom) | relative strength (%) |
|---|---|---|
| 13.8° ± 0.2° | 6.41 | 17.4 |
| 16.0° ± 0.2° | 5.53 | 12.8 |
| 17.1° ± 0.2° | 5.17 | 14.3 |
| 21.6° ± 0.2° | 4.10 | 20.6 |
| 22.1° ± 0.2° | 4.02 | 47.7 |
| 22.5° ± 0.2° | 3.95 | 100.0 |
| 23.7° ± 0.2° | 3.75 | 17.6 |
| 24.7° ± 0.2° | 3.59 | 27.6 |
| 31.7° ± 0.2° | 2.81 | 25.2. |

3. The medicament of containing the crystal of claim 1, wherein the medicament is an inhibitor of adenylate cyclase 1.

4. The medicament of claim 3, wherein the medicament is an analgesic.

5. The medicament of claim 4, wherein the analgesic is a medicament for the treatment of neuropathic pain and/or inflammatory pain.

6. The medicament of claim 4, wherein the analgesic is a medicament for the treatment of cancerous pain.

7. The medicament of claim 3, wherein the medicament is a medicament for the treatment of anxiety caused by the neuropathic pain and other disease-related anxiety and depression.

8. The medicament of claim 3, wherein the medicament is a medicament for the treatment of chronic visceral pain and anxiety and depression associated thereto.

9. The medicament of claim 5, wherein the analgesic is a medicament for the treatment of cancerous pain.

10. A medicament containing the crystal of claim 2.

11. The medicament of claim 10, wherein the medicament is an inhibitor of adenylate cyclase 1.

12. The medicament of claim 11, wherein the medicament is an analgesic.

13. The medicament of claim 12, wherein the analgesic is a medicament for the treatment of neuropathic pain and/or inflammatory pain.

14. The medicament of claim 12, wherein the analgesic is a medicament for the treatment of cancerous pain.

15. The medicament of claim 13, wherein the analgesic is a medicament for the treatment of cancerous pain.

16. The medicament of claim 10, wherein the medicament is a medicament for the treatment of anxiety caused by the neuropathic pain and other disease-related anxiety and depression.

17. The medicament of claim 10, wherein the medicament is a medicament for the treatment of chronic visceral pain and anxiety and depression associated thereto.

* * * * *